(12) United States Patent
Burgett et al.

(10) Patent No.: US 10,194,233 B2
(45) Date of Patent: *Jan. 29, 2019

(54) EARPHONES AND EARBUDS WITH PHYSIOLOGIC SENSORS

(71) Applicant: Harman International Industries, Incorporated, Stamford, CT (US)

(72) Inventors: Seth D. Burgett, Glen Carbon, IL (US); Aaron Gorga, St. Louis, MO (US); Effrosini A. Karayiannis, St. Louis, MO (US)

(73) Assignee: Harman International Industries, Incorporated, Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/408,061

(22) Filed: Jan. 17, 2017

(65) Prior Publication Data

US 2017/0127174 A1    May 4, 2017

Related U.S. Application Data

(63) Continuation of application No. 13/891,230, filed on May 10, 2013, now Pat. No. 9,591,395.
(Continued)

(51) Int. Cl.
*H04R 1/10* (2006.01)
*A61B 5/00* (2006.01)
(Continued)

(52) U.S. Cl.
CPC ......... *H04R 1/1091* (2013.01); *A61B 5/6817* (2013.01); *A61F 13/2017* (2013.01);
(Continued)

(58) Field of Classification Search
CPC .............. H04R 2460/13; H04R 1/1091; H04R 1/1016; H04R 1/105; H04R 1/10;
(Continued)

(56) References Cited

U.S. PATENT DOCUMENTS 5,673,692 A    10/1997  Schulze et al.
8,157,730 B2    4/2012  LeBoeuf et al.
(Continued)

FOREIGN PATENT DOCUMENTS

CN    101247668 A    8/2008
CN    202068541 U    12/2011
(Continued)

OTHER PUBLICATIONS

Extended European Search Report for Application No. 13787450, dated Feb. 22, 2016, 8 pages.
(Continued)

*Primary Examiner* — Leshui Zhang
(74) *Attorney, Agent, or Firm* — Brooks Kushman P.C.

(57) ABSTRACT

An earphone with a physiologic sensor includes a housing; a speaker in the housing; an enhancer comprising a body mounted on the housing and adapted to be secured in the ear to acoustically couple the speaker to the user's ear; and an optical physiologic sensor disposed inside the enhancer, the enhancer having an aperture or window aligned with the optical physiologic sensor, so that the sensor can optically couple with the user's ear when the enhancer is secured in the user's ear.

15 Claims, 7 Drawing Sheets

Related U.S. Application Data (60) Provisional application No. 61/645,722, filed on May 11, 2012.

(51) Int. Cl.
   *A61F 13/20* (2006.01)
   *A61B 5/01* (2006.01)
   *A61B 5/02* (2006.01)

(52) U.S. Cl.
   CPC ........... *H04R 1/105* (2013.01); *H04R 1/1016* (2013.01); *A61B 5/01* (2013.01); *A61B 5/02* (2013.01); *A61B 2562/0219* (2013.01); *A61B 2562/0247* (2013.01); *A61B 2562/0271* (2013.01); *A61B 2562/043* (2013.01); *A61B 2562/046* (2013.01); *A61B 2562/066* (2013.01); *A61B 2562/16* (2013.01)

(58) Field of Classification Search
   CPC .... H04R 1/1008; H04R 1/1083; H04R 25/00; H04R 25/407; H04R 25/60; H04R 25/606; H04R 25/602; H04R 25/652; H04R 25/70; H04R 2420/07; H04R 2225/021; H04R 2225/023; H04R 2225/025; H04R 2225/63; H04R 5/0335; H04R 17/005; A61B 5/6817; A61B 5/0476; A61B 5/01; A61B 5/02055; A61B 5/121; A61B 2562/0219; A61B 2562/0247; A61B 2562/0271; A61B 5/00; A61B 5/02; A61B 5/1455; A61B 5/145; A61B 5/11; H04M 1/6066; H04M 1/72558; H04M 2250/12; H04M 15/00; H04W 4/02; H04N 7/18
   USPC .... 381/72, 74, 309, 23.1, 60, 312, 314, 315, 381/322, 323, 324, 325, 326, 328, 329, 381/330, 150, 151, 337, 338, 339, 367, 381/376, 380, 381, 111, 116, 117, 3, 28; 455/575.2, 405, 456.3; 700/94; 600/300–301, 309, 310, 340, 322, 323, 600/324, 344, 559; 340/573.1; 348/77, 348/E07.085
   See application file for complete search history.

(56) References Cited

U.S. PATENT DOCUMENTS

| | | |
|---|---|---|
| D666,169 S | 8/2012 | Tucker et al. |
| 8,251,903 B2 | 8/2012 | LeBoeuf et al. |
| 8,320,982 B2 | 11/2012 | LeBoeuf et al. |
| 8,323,982 B2 | 12/2012 | LeBoeuf et al. |
| 8,647,270 B2 | 2/2014 | LeBoeuf et al. |
| 8,652,040 B2 | 2/2014 | LeBoeuf et al. |
| 8,700,111 B2 | 4/2014 | LeBoeuf et al. |
| 2008/0076972 A1 | 3/2008 | Dorogusker et al. |
| 2008/0205679 A1* | 8/2008 | Darbut ................ H04R 25/554 381/328 |
| 2009/0112071 A1* | 4/2009 | LeBoeuf ............. A61B 5/02116 600/301 |
| 2009/0112100 A1 | 4/2009 | Shioi |
| 2010/0217098 A1 | 8/2010 | LeBoeuf et al. |
| 2010/0217099 A1 | 8/2010 | LeBoeuf et al. |
| 2010/0217100 A1 | 8/2010 | LeBoeuf et al. |
| 2010/0217102 A1* | 8/2010 | LeBoeuf ................. A61B 5/00 600/310 |
| 2010/0217103 A1* | 8/2010 | Abdul-Hafiz ...... A61B 5/14552 600/322 |
| 2010/0256460 A1 | 10/2010 | Haveri et al. |
| 2010/0298727 A1 | 11/2010 | Uenishi et al. |
| 2011/0268308 A1* | 11/2011 | Vasquez ............... H04R 1/1016 381/380 |
| 2012/0197093 A1* | 8/2012 | LeBoeuf ................ G16H 40/63 600/301 |
| 2013/0131519 A1 | 5/2013 | LeBoeuf et al. |
| 2014/0114147 A1 | 4/2014 | Romesburg |
| 2014/0128690 A1 | 5/2014 | LeBoeuf |

FOREIGN PATENT DOCUMENTS

| | | | |
|---|---|---|---|
| EP | 1475035 A1 | 11/2004 | |
| EP | 2077091 A2 | 7/2009 | |
| JP | 5788383 | 11/1955 | |
| JP | 61200003 U | 12/1986 | |
| JP | 5384520 A | 4/1988 | |
| JP | 05064296 A | * 3/1993 | .......... H04R 25/652 |
| JP | H09253062 A | 9/1997 | |
| JP | 2008136556 A | 6/2008 | |
| JP | 2009502298 A | 1/2009 | |
| JP | 05064296 B2 | 8/2012 | |
| WO | 2005020841 A2 | 3/2005 | |
| WO | 2007013054 A1 | 2/2007 | |

OTHER PUBLICATIONS

International Search Report for Application No. PCT/US2013/040471, dated Jul. 26, 2013, 1 page.

Japanese Office Action and English translation for Application No. 2015-511726, dated Mar. 1, 2017, 16 pages.

* cited by examiner

EARPHONES AND EARBUDS WITH PHYSIOLOGIC SENSORS

CROSS-REFERENCE TO RELATED APPLICATIONS

This application is a continuation of U.S. application Ser. No. 13/891,230 filed May 10, 2013, which, in turn, claims the benefit of U.S. provisional application Ser. No. 61/645,722 filed May 11, 2012, the disclosures of which are hereby incorporated in their entirety by reference herein.

TECHNICAL FIELD

This invention relates to earphones and earbuds, and in particular, to earphone or earbuds that incorporate physiologic sensors.

BACKGROUND

This section provides background information related to the present disclosure which is not necessarily prior art.

It is increasingly common for people to monitor their physiology while exercising. Exercise machines often include heart rate monitors to measure the user's heart rate, but these of course require the user to remain stationery at the machine. Chest straps to monitor heart rate and/or respiration of an athlete have been developed, but these can be cumbersome and uncomfortable and therefore, are not widely used.

Recently, developments in ear-based physiologic monitors have demonstrated their acceptability for medical applications. Attempts have been made to incorporate these sensors into earbuds and earphones. See for example, LeBoeuf, et al., U.S. Pat. No. 8,157,730, for Physiological and Environmental Monitoring Systems and Methods. However, maintaining the sensors in proper position for consistent and accurate monitoring remains a challenge.

SUMMARY

This section provides a general summary of the disclosure, and is not a comprehensive disclosure of its full scope or all of its features.

Generally, embodiments of the present invention provide a combination earphone and physiologic sensor, in some embodiments, the earphone is of the type comprising a housing with a speaker therein, and an enhancer for engaging the user's ear, and acoustically coupling the speaker with the user's ear. A physiologic sensor is disposed on or preferably in the enhancer. The enhancer can have at least one aperture or window therein, so that the sensor can optically couple to the ear of the wearer to provide physiologic data.

In other embodiments, the earphone and physiologic sensor combination comprises an earphone with an earloop. A transmitter is provided on one of the earphone and the earloop, and a receiver is provided on the other of the earphone and earloop. The physiologic sensor can sense physiologic properties through optical transmission through a part of the ear between the transmitter and the receiver.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
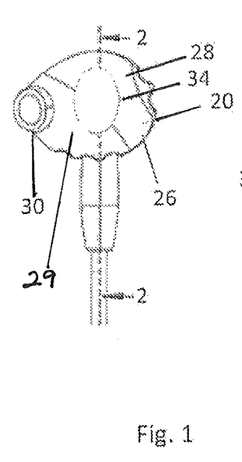
FIG. 1 is a front elevation view of an earbud or earphone constructed according to the principles of this invention.
Figure 2:
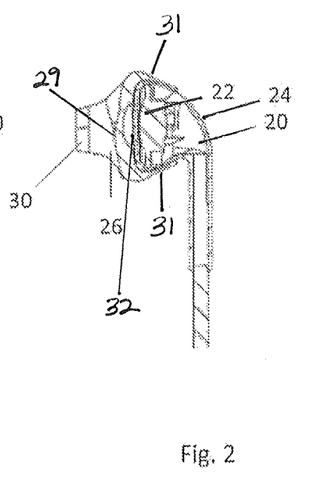
FIG. 2 is cross-sectional view of the earbud or earphone, taken along the plane of line 2-2 in FIG. 1.
Figure 3:
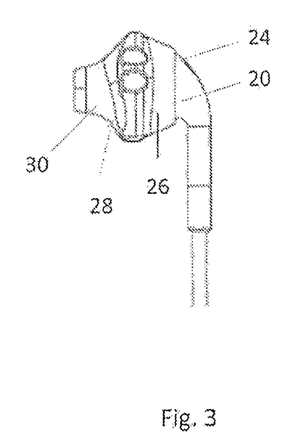
FIG. 3 is an end elevation view of an earbud or earphone constructed according to the principles of this invention.
Figure 4:
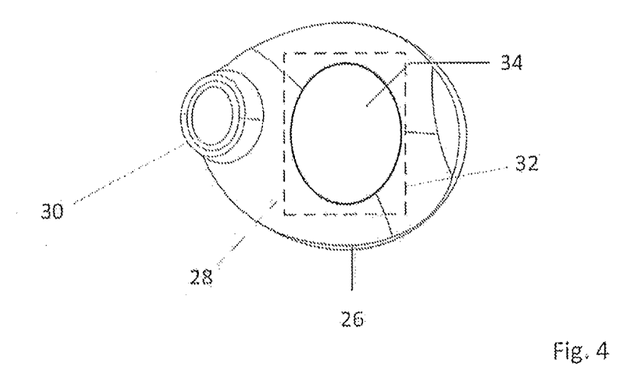
FIG. 4 is a front elevation view of a first preferred embodiment of an enhancer constructed according to the principles of this invention.

A first embodiment of an earphone and physiologic sensor in accordance with the principles of this invention is indicated generally as 20 in FIGS. 1-3. The earphone and sensor combination 20 comprises a speaker 22 in a housing 24. An enhancer 26 comprising a body 28 adapted to fit within the ear of the user. The body 28 has an opening for receiving a portion of the housing 24, so that the speaker 22 communicates with the interior of the body. The body 28 has a front outer wall 29 and adjoining side walls 31, the front outer wall 29 spaced from the housing 24 and the side walls 31 contacting the housing 24. A sound tube 30 projects from the body 28, and is adapted to fit in the user's ear canal, to deliver sound produced by the speaker 22 in the body 28, to the user's ear.

In accordance with the principles of this invention, the earphone and sensor combination 20 further comprises an optical physiologic sensor 32. In this first embodiment, the physiologic sensor 32 is disposed in the body 28 beneath the front outer wall 29, and there is an aperture 34 in the front outer wall 29 of the body 28 that faces the user's ear when the earphone is fitted in the user's ear. The aperture 34 is shown as oval shaped, but it could be some other shape and size. The aperture 34 optically connects the physiologic sensor 32 with the user's ear, so that it can measure one or more physiological properties, for example, pulse and/or O2 saturation, or any other physiologic property that can be measured in this manner. The physiologic sensor 32 may include other associated sensors, not shown, for example, a temperature sensor for sensing ambient temperature, gps sensor, pressure sensor, and/or altimeter, accelerometer for measuring steps.

Figure 5:
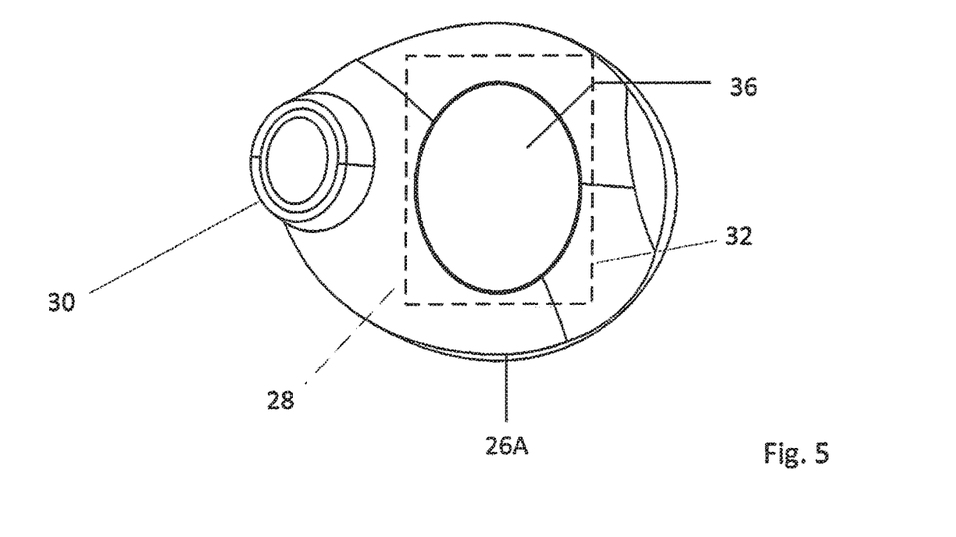
FIG. 5 is a front elevation view of a second preferred embodiment of an enhancer constructed according to the principles of this invention.

In accordance with a second preferred embodiment of the enhancer indicated as 26A in FIG. 5, instead of the aperture 34 in the wall of the body of the enhancer, there is a window 36. The window 36 can be a portion of the wall that is thinned sufficiently that the physiologic sensor 32 can optically connect with the user's ear. Alternatively, the window 36 can be a portion of the wall that is transparent to the wavelengths used by the physiologic sensor 32. This window 36 can be co-molded when the body is formed, or it can be formed separately, and inserted into the wall and secured for example, with adhesive, sonic welding, or other suitable means. The window 36 is shown as oval shaped, but it could be some other shape and size. Otherwise, the enhancer 26A is preferably like enhancer 26, and the other parts of an earphone and physiologic sensor incorporating the enhancer 26A are similar to the earphone and physiologic sensor combination 20.

Figure 6:
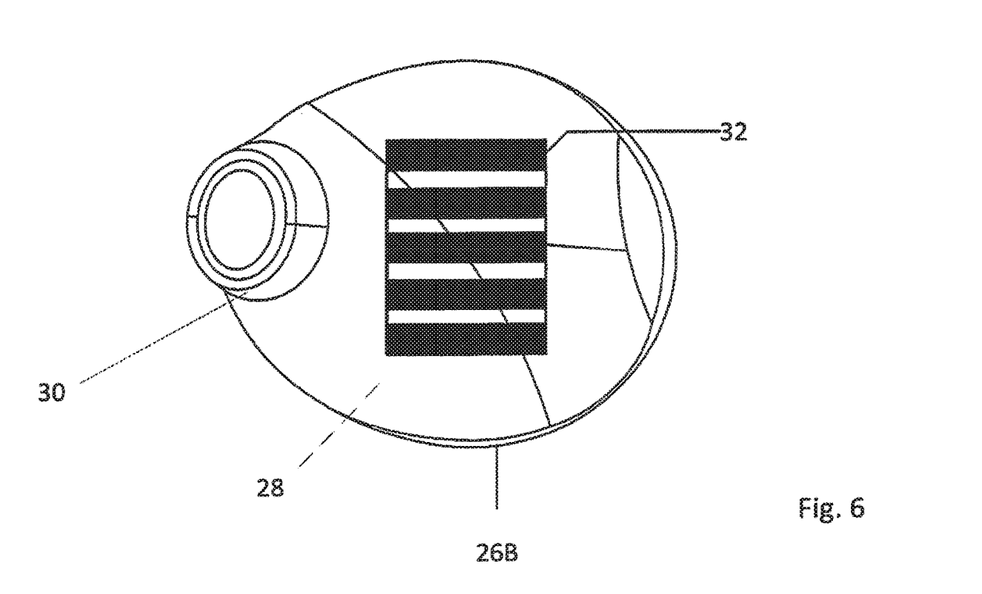
FIG. 6 is a front elevation view of a third preferred embodiment of an enhancer constructed according to the principles of this invention.

In accordance with a third preferred embodiment of the enhancer indicated as 26B in FIG. 6, instead of the aperture 34 or window 36 in the wall of the body of the enhancer, the physiologic sensor 32 is mounted on the exterior of the enhancer 26B to optically connect with the user's ear. Otherwise, the enhancer 26B is preferably like enhancer 26, and the other parts of an earphone and physiologic sensor incorporating the enhancer 26B are similar to the earphone and physiologic sensor combination 20.

Figure 7:
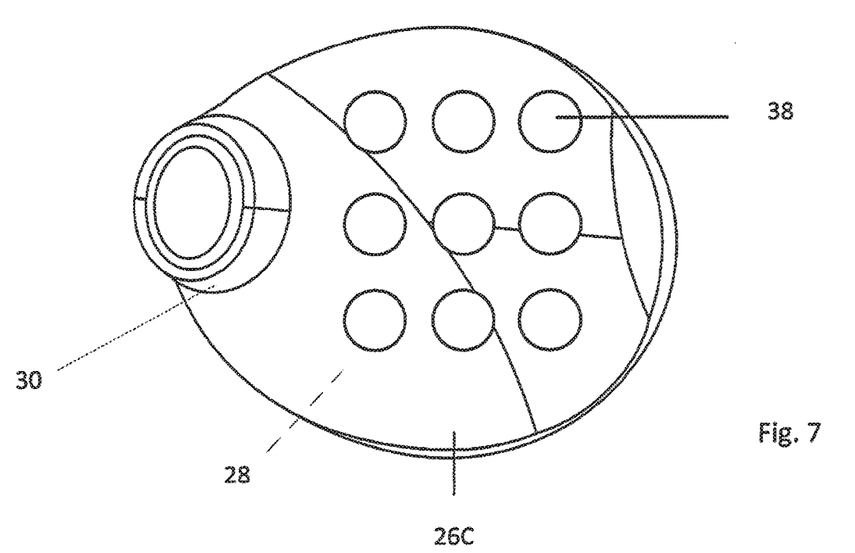
FIG. 7 is a front elevation view of a fourth preferred embodiment of an enhancer constructed according to the principles of this invention.

In accordance with a fourth preferred embodiment of the enhancer indicated as 26C in FIG. 7, the face of the body 28 has a plurality of apertures 38, instead of just one as enhancer 26. In this fourth preferred embodiment, there are nine generally circular apertures 38, arranged in a three-by-three array. The apertures 38 could have some other shape, and there could be fewer or more than nine such apertures. Individual sensors can be provided for each aperture, or a single sensor can be provided with the apertures providing multiple accesses for the single sensor. Rather than apertures 38, windows of similar shape, size, and arrangement can be provided. These windows would preferably be like the window 36, described above. Otherwise, the enhancer 26C is preferably like enhancer 26, and the other parts of an earphone and physiologic sensor incorporating the enhancer 26C are similar to the earphone and physiologic sensor combination 20.

Figure 8:
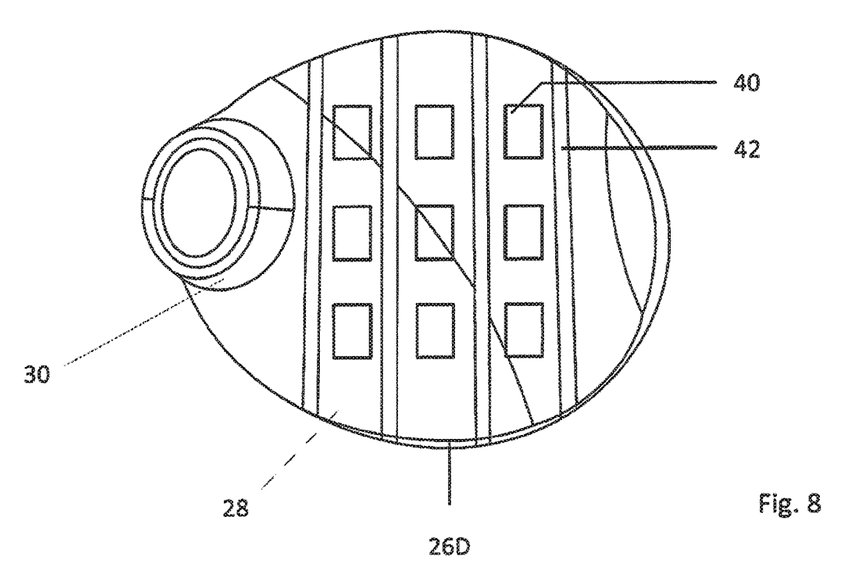
FIG. 8 is a front elevation view of a fifth preferred embodiment of an enhancer constructed according to the principles of this invention.

In accordance with a fifth preferred embodiment of the enhancer indicated as 26D in FIG. 8, the face of the body 28 has a plurality of windows 40, instead of just one as enhancer 26A. In this fifth preferred embodiment, there are nine generally rectangular windows 40, arranged in a three-by-three array. The windows 40 could have some other shape, and there could be fewer or more than nine such windows. Individual sensors can be provided for each window, or a single sensor can be provided with the windows providing multiple accesses for the single sensor. Rather than windows 40, apertures of similar shape, size, and arrangement can be provided. These apertures would preferably be like the aperture 34, described above. The enhancer 26D also includes channels 42 for conducting sweat away from the windows 40 to reduce the interference with the optical connection between the sensor(s) and the user's ear. While four channels 42 are shown in FIG. 8, there can be fewer or more channels and they can be oriented differently to improve their ability to conduct sweat away from the windows. The channels 42 can be sized to conduct sweat by capillary action, and can be formed from, or their surfaces can be treated with hydrophilic and/or hydrophobic materials to facilitate their sweat conduction ability. Otherwise, the enhancer 26D is preferably like enhancer 26, and the other parts of an earphone and physiologic sensor incorporating the enhancer 26D are similar to the earphone and physiologic sensor combination 20.

Figure 9:
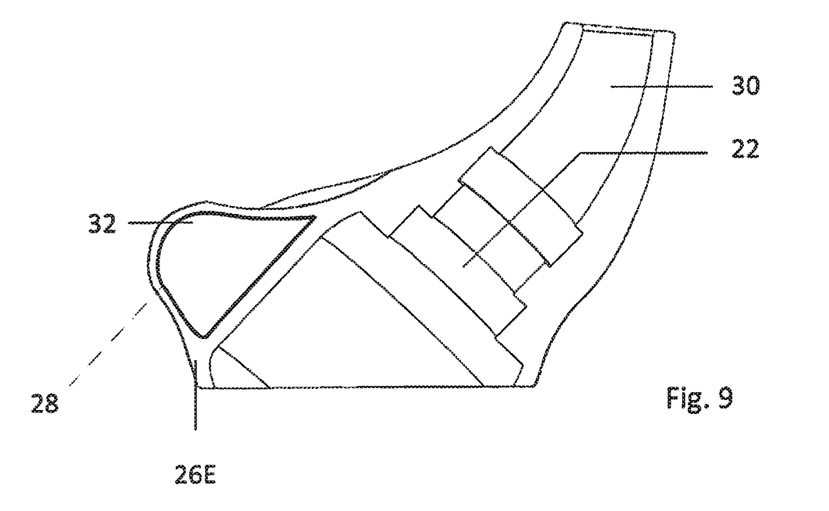
FIG. 9 is a cross-sectional view of a sixth preferred embodiment of an enhancer constructed according to the principles of this invention.

In accordance with a sixth preferred embodiment of the enhancer indicated as 26E in FIG. 9, the body 28 is shown with a speaker 22 disposed entirely therein, and aligned with the sound tube 30. FIG. 9 illustrates that even where the speaker is entirely contained in the enhancer 26E, there is adequate space in the enhancer to accommodate a physiologic sensor 32.

Figure 10:
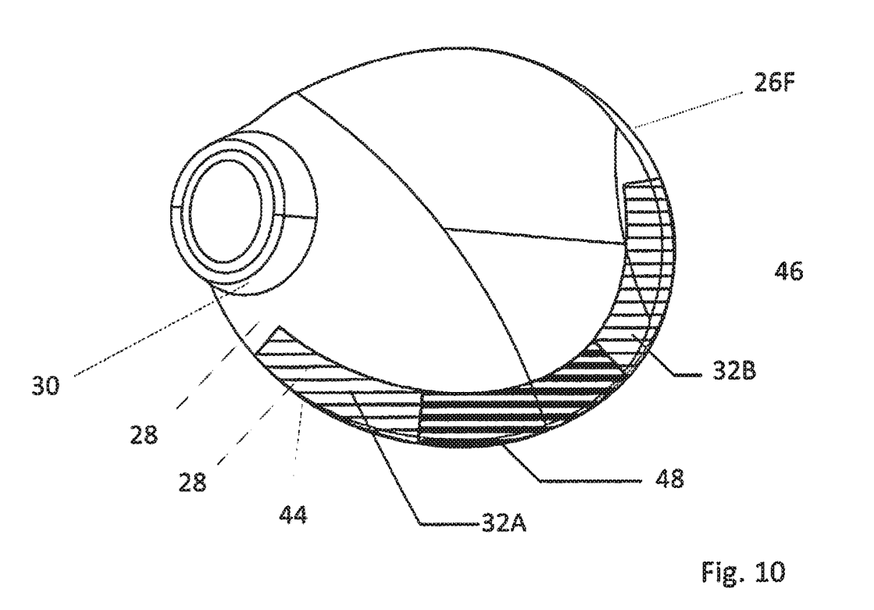
FIG. 10 is a front elevation view of a seventh preferred embodiment of an enhancer constructed according to the principles of this invention.
Figure 11:
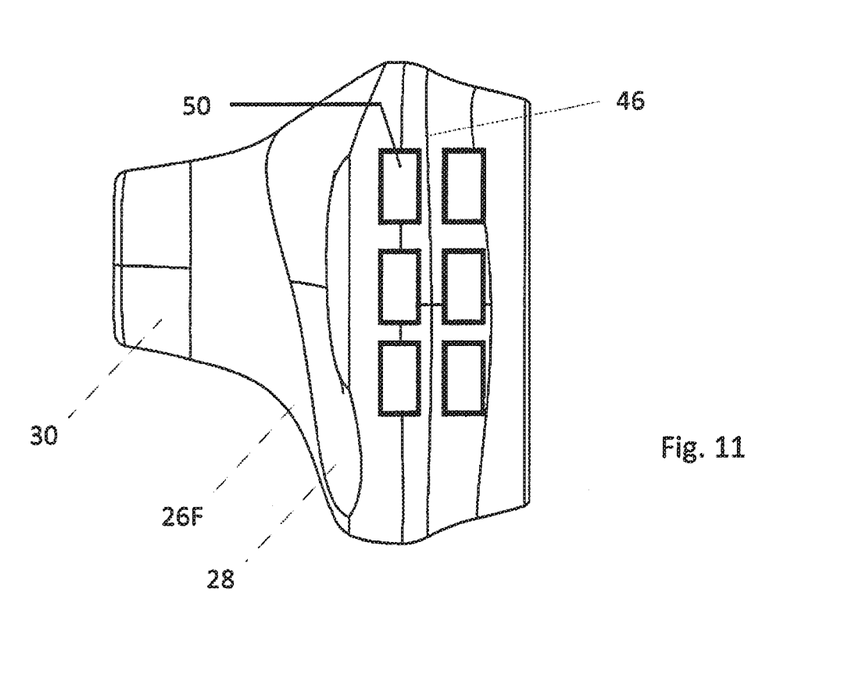
FIG. 11 is a rear end elevation view of the enhancer of FIG. 10.
Figure 12:
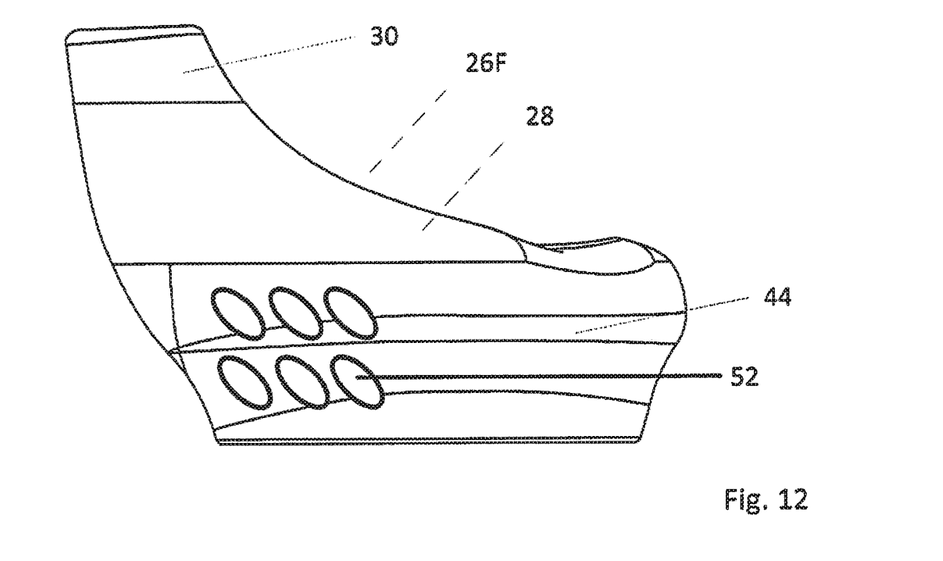
FIG. 12 is a bottom plan view of the enhancer of FIG. 10.

In accordance with a seventh preferred embodiment of the enhancer indicated as 26F in FIGS. 10-12, the lower edge 44 of the enhancer 26F has a physiologic sensor 32A and the back edge 46 of the enhancer has a physiologic sensor 32B. A sweat management system 48 can be provided at the bottom of the enhancer 26F to either redirect or absorb sweat to reduce interference with the sensors 32A and 32B.

As shown in FIG. 11, the enhancer 26F can have a plurality of windows 50 in the back edge 46, so that the physiologic sensor 32B can optically couple to the forward-facing portions of the user's ear. In this seventh preferred embodiment, there are six generally rectangular windows 50, arranged in a two-by-three array. The windows 50 could have some other shape and size, and there could be fewer or more than six such windows. Individual sensors can be provided for each window, or a single sensor can be provided with the windows providing multiple accesses for the single sensor. The windows 50 may be like window 36, described above. Rather than windows 50, apertures of similar shape, size, and arrangement can be provided. These apertures would preferably be like the aperture 34, described above.

As shown in FIG. 12, the enhancer 26F can have a plurality of windows 52 in the lower edge 44, so that the physiologic sensor 32A can optically couple to the upward-facing portions of the user's ear. In this seventh preferred embodiment, there are six generally circular windows 52, arranged in a two by three array. The windows 52 could have some other shape and size, and there could be fewer or more than six such windows. Individual sensors can be provided for each window, or a single sensor can be provided with the windows providing multiple accesses for the single sensor. The windows 52 may be like window 36, described above. Rather than windows 52, apertures of similar shape, size, and arrangement can be provided. These apertures would preferably be like the aperture 34, described above.

The sweat management system 48 can be provided at the bottom of the enhancer 26F, to either redirect or absorb sweat to reduce interference with the sensors 32A and 32B. The sweat management system 48 can comprise a plurality of channels, like channels 42 discussed above, to conduct sweat away from the windows 50 and 52. Alternatively, the sweat management system 48 can comprise a wicking material that conducts sweat away from the windows 50 and 52. The sweat management system 48 can include a reservoir for holding sweat conducted away from the windows 50 and 52. This reservoir can comprise a hollow space, but preferably comprises a hydrogel that can reversibly absorb sweat and dry out.

Figure 13:
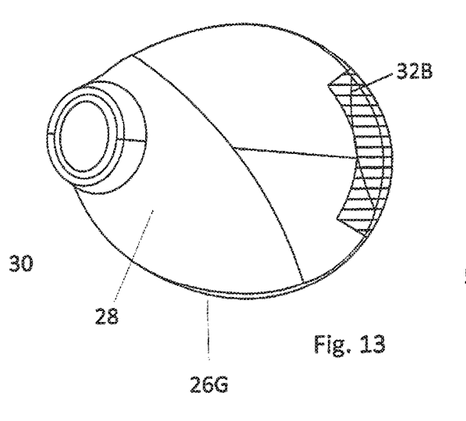
FIG. 13 is a front elevation view of an eighth preferred embodiment of an enhancer constructed according to the principles of this invention.
Figure 14:
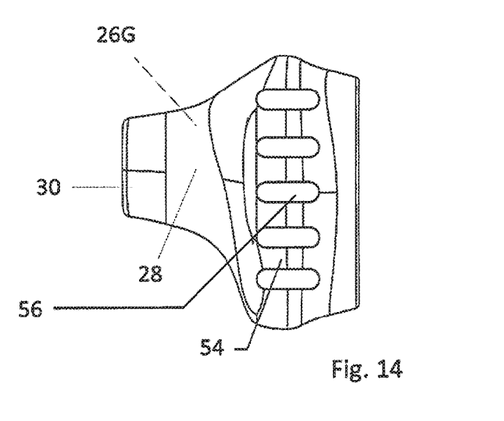
FIG. 14 is a rear end elevation view of the enhancer of FIG. 13.

The enhancer 26F can have physiologic sensor 32A and windows 52 and physiologic sensor 32B and windows 50, as shown and described, or the enhancer can have just one of physiologic sensor 32A and windows 52 or physiologic sensor 32B and windows 50. For example, as shown in FIGS. 13 and 14, an eighth preferred embodiment of an enhancer 26G includes a physiologic sensor 32B adjacent the rearward edge 54. The enhancer 26G has a plurality of windows 56 in the rearward edge 54, so that the physiologic sensor 32B is optically connected to the forwardly facing portion of the user's ear.

Figure 15:
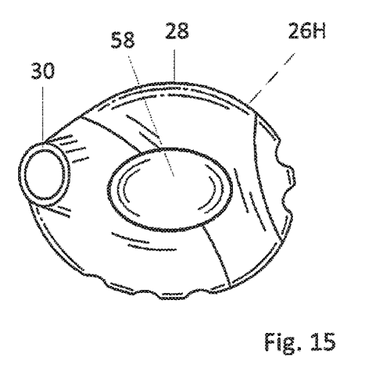
FIG. 15 is a front elevation view of a ninth preferred embodiment of an enhancer constructed according to the principles of this invention.
Figure 16:
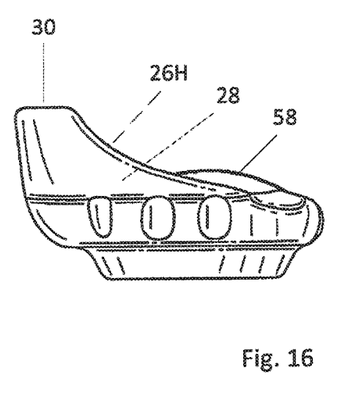
FIG. 16 is a bottom plan view of the enhancer of FIG. 15.

In accordance with a ninth preferred embodiment of the enhancer indicated as 26H in FIG. 15, the face of the body 28 has a pillow 58 over a window in the face of the body. The pillow 58 is preferably pliable to engage the surface of the user's ear, and by this engagement provide optical coupling of the sensor, and exclusion of sweat. This pillow 58 may be formed by a gel-filled membrane that is translucent to the optical wavelengths used by the sensor. This pillow 58 may alternatively be a patch of a hydrogel, which when exposed to moisture, such as from water or sweat, swells to form a compliant mass translucent to the optical wavelengths used by the sensor. Otherwise the enhancer 26H is preferably like enhancer 26, and the other parts of an earphone and physiologic sensor incorporating the enhancer 26H are similar to the earphone and physiologic sensor combination 20.

Figure 17:
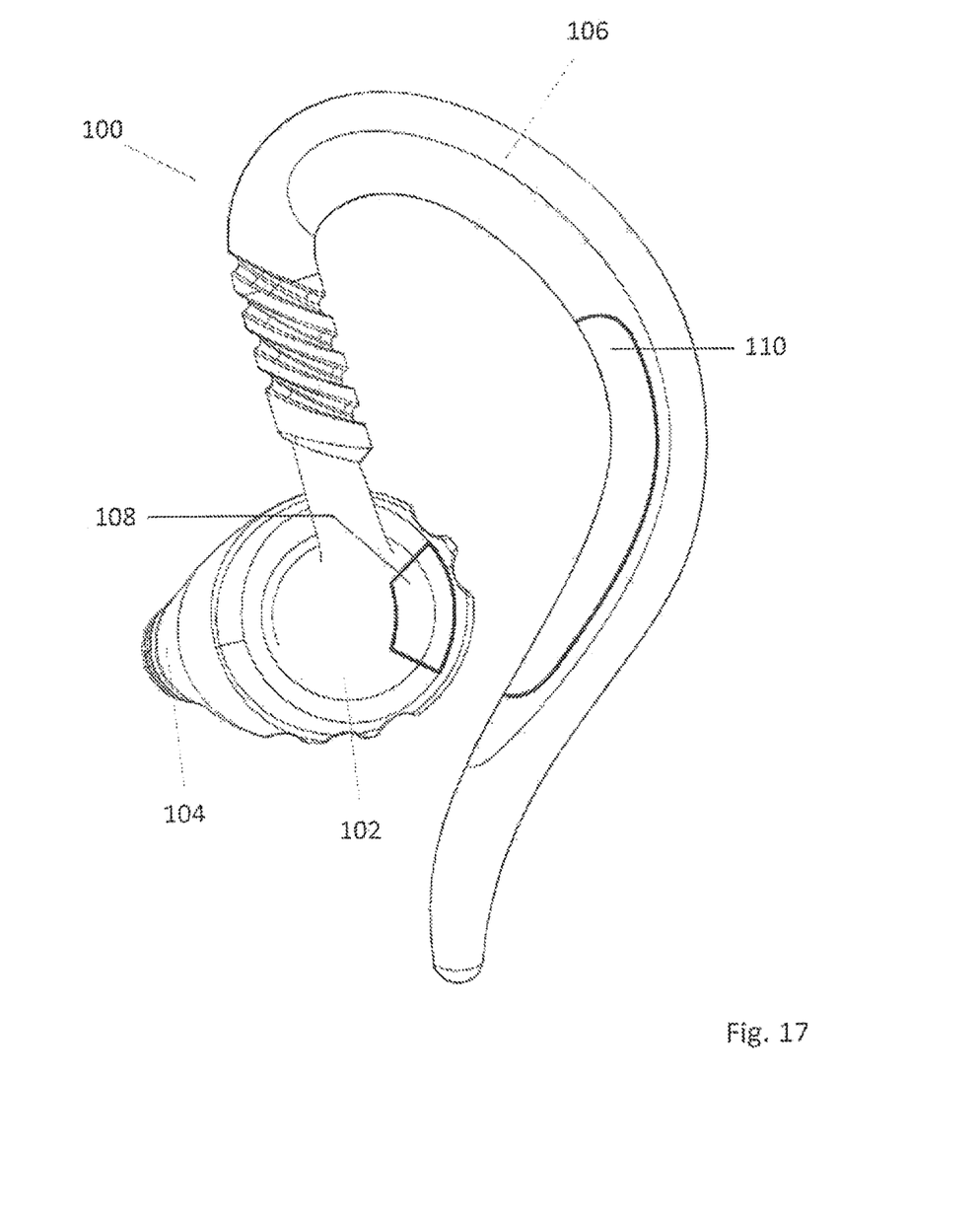
FIG. 17 is a rear elevation view of a tenth preferred embodiment of an enhancer constructed according to the principles of this invention.

An earphone and physiologic sensor in accordance with a tenth embodiment of the principles of this invention, is indicated generally as 100 in FIG. 17. The earphone and physiologic sensor 100 comprises a housing 102 containing a speaker (not shown), and an enhancer 104 for coupling the speaker to the user's ear. The earphone comprises an earloop 106 for engaging the user's ear. The earphone and physiologic sensor 100 further comprises a transmitter 108 on the housing 102 and a receiver 104 on the earloop 106. The transmitter 108 and receiver 110 operate to sense physiologic properties of the user. Alternatively, the transmitter can be on the earloop 106 and the receiver 110 can be on the housing 102.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An earphone, comprising:
a housing;
a speaker in the housing;
an enhancer comprising a body mounted on the housing and adapted to be secured in a user's ear to acoustically couple the speaker to the user's ear, the body having a front outer wall and adjoining side walls, the front outer wall spaced from the housing and the side walls contacting the housing;
a sound tube projecting from and above the front outer wall of the body and adapted to fit in a user's ear canal; and
an optical physiologic sensor disposed inside the enhancer beneath the front outer wall of the body adjacent the sound tube, and at least one aperture in the front outer wall of the body adjacent the sound tube and aligned with the optical physiologic sensor, so that the optical physiologic sensor can optically couple with the user's ear external to the front outer wall when the enhancer is secured in the user's ear.

2. The earphone according to claim 1, wherein there are a plurality of apertures, arranged in an array.

3. The earphone according to claim 1, wherein the at least one aperture is in the portion of the enhancer that faces the concha of the user's ear.

4. The earphone according to claim 1 wherein the at least one aperture is in a portion of the enhancer that faces the upwardly facing wall of the concha of the user's ear.

5. The earphone according to claim 1 wherein the at least one aperture is in a portion of the enhancer that faces the forwardly facing wall of the concha of the user's ear.

6. The earphone according to claim 1 further comprising at least one channel in the outer surface of the enhancer for directing sweat away from the at least one aperture.

7. The earphone according to claim 1 further comprising an absorbent patch for absorbing sweat from adjacent the at least one aperture.

8. An earphone, comprising:
a housing;
a speaker in the housing;
an enhancer comprising a body mounted on the housing and adapted to be secured in a user's ear to acoustically couple the speaker to the user's ear, the body having a front outer wall and adjoining side walls, the front outer wall spaced from the housing and the side walls contacting the housing;
a sound tube projecting from and above the front outer wall of the body and adapted to fit in a user's ear canal; and
an optical physiologic sensor disposed inside the enhancer beneath the front outer wall of the body adjacent the sound tube, and at least one window in the front outer wall of the body adjacent the sound tube and aligned with the optical physiologic sensor, so that the optical physiologic sensor can optically couple with the user's ear external to the front outer wall when the enhancer is secured in the user's ear.

9. The earphone according to claim 8 wherein there are a plurality of windows, arranged in an array.

10. The earphone according to claim 8 wherein the at least one window is in the portion of the enhancer that faces the concha of the user's ear.

11. The earphone according to claim 8 wherein the at least one window is in a portion of the enhancer that faces the upwardly facing wall of the concha of the user's ear.

12. The earphone according to claim 8 wherein the at least one window is in a portion of the enhancer that faces the forwardly facing wall of the concha of the user's ear.

13. The earphone according to claim 8 further comprising at least one channel in a surface of the enhancer for directing sweat away from the at least one aperture.

14. The earphone according to claim 8 further comprising an absorbent patch for absorbing sweat from adjacent the at least one window.

15. An earphone, comprising:
   a housing;
   a speaker in the housing;
   an enhancer comprising a body mounted on the housing and adapted to be secured in a user's ear to acoustically couple the speaker to the user's ear, the body having a front outer wall and adjoining side walls, the front outer wall spaced from the housing and the side walls contacting the housing;
   a sound tube projecting from and above the front outer wall of the body and adapted to fit in a user's ear canal; and
   an optical physiologic sensor disposed inside the enhancer beneath the front outer wall of the body adjacent the sound tube, and a deformable pillow on the front outer wall of the body adjacent the sound tube and aligned with the optical physiologic sensor, the deformable pillow being transparent to optical wavelengths used by the optical physiologic sensor, the deformable pillow contacting and conforming to the user's ear, so that the optical physiologic sensor can optically couple with the user's ear external to the front outer wall when the enhancer is secured in the user's ear.

* * * * *